US00PP33445P3

(12) United States Plant Patent
Slaughter et al.

(10) Patent No.: US PP33,445 P3
(45) Date of Patent: Sep. 7, 2021

(54) PLUM TREE NAMED 'WAPLUMONE'

(50) Latin Name: *Prunus salicina*
Varietal Denomination: Waplumone

(71) Applicant: Wawona Packing Co, LLC, Cutler, CA (US)

(72) Inventors: John Keith Slaughter, Fresno, CA (US); Kaylan M. Roberts, Fresno, CA (US)

(73) Assignee: Wawona Packing Co., LLC, Cutler, CA (US)

( * ) Notice: Subject to any disclaimer, the term of this patent is extended or adjusted under 35 U.S.C. 154(b) by 0 days.

(21) Appl. No.: 16/602,859

(22) Filed: Dec. 11, 2019

(65) Prior Publication Data

US 2021/0185868 P1 Jun. 17, 2021

(51) Int. Cl.
*A01H 5/08* (2018.01)
*A01H 6/74* (2018.01)

(52) U.S. Cl.
USPC ..... Plt./184
CPC ..... *A01H 6/7472* (2018.05)

(58) Field of Classification Search
USPC ..... Plt./184
CPC ..... A01H 5/0862
See application file for complete search history.

*Primary Examiner* — Kent L Bell
(74) *Attorney, Agent, or Firm* — Potter Anderson and Corroon LLP

(57) ABSTRACT

A new and distinct variety of plum tree (*Prunus salicina*), which is denominated varietally as 'Waplumone', and which produces an attractively colored red-fleshed, freestone plum which is mature for harvesting and shipment approximately July 2 to July 12 under the ecological conditions prevailing in the San Joaquin Valley of central California.

1 Drawing Sheet

Botanical designation: *Prunus salicina.*
Varietal denomination: 'Waplumone'.

BACKGROUND OF THE NEW VARIETY

The present variety of plum tree resulted from an ongoing program of fruit tree breeding. The purpose of this program is to improve the commercial quality of deciduous fruit varieties, and rootstocks, by creating and releasing promising selections of *Prunus* species. To this end we make both controlled and hybrid cross pollinations each year to produce seedling populations from which improved progenies are evaluated and selected.

The seedling, 'Waplumone' was originated and selected from a population of seedlings growing in experimental orchards located near Fowler, Calif. The seedlings, from which the current variety was derived were grown on their own roots, derived from planting seed of 'Wickson' plum (unpatented), which was used as the female parent. The pollen parent of this seedling is unknown. The resulting fruit was collected from the female parent at a mature stage, and seeds were extracted in August of 1998. After a period of stratifcation, the seed was placed in the greenhouse by population and then field planted for tree establishment and ultimately to exhibit fruit for evaluation. One red-fleshed plum seedling, which is the present variety, exhibited especially desirable characteristics and was then designated as 'D54.064'. This seedling was marked for subsequent observation. After the 2003 fruiting season, the new variety of plum tree was selected for advanced evaluation and repropagation.

ASEXUAL REPRODUCTION

Asexual reproduction of this new and distinct variety of plum tree was accomplished by budding the new plum tree onto 30 trees of 'Nemaguard' Rootstock (unpatented). This was performed by the breeders in an experimental orchard located near Fowler, Calif. Subsequent evaluations of these asexually reproduced plants have shown those asexual reproductions run true to the original tree. All characteristics of the original tree and its fruit were established and are transmitted through these succeeding asexual propagations.

SUMMARY OF VARIETY

'Waplumone' is a new and distinct variety of plum tree, which is considered of medium sized fruit, and which has a moderately vigorous growth characteristic. This new tree is also a regular and productive bearer of relatively firm, red-fleshed, medium acid, and freestone fruit that have a very good flavor and eating qualities.

This new plum tree has a medium chilling requirement of approximately 500 hours and further produces relatively uniformly sized fruit throughout the tree's canopy. In addition to the foregoing, the fruit of the new plum also appears to have good handling and shipping qualities. The 'Waplumone' plum tree bears fruit which are typically ripe for commercial harvesting and shipment on approximately July 2 to July 12 under the ecological conditions prevailing in the San Joaquin Valley of central California. In relative comparison to the 'Wickson' plum tree (Luther Burbank introduction 19$^{th}$ century), which is the seed parent of and closest comparison cultivar to the present variety, 'Waplumone' ripens approximately 10 to 14 days earlier than the 'Wickson' plum tree. Further, the current variety produces fruit that is firmer and more uniformly and oblately shaped and exhibits approximately 5.0 to 7.0 brix higher than the 'Wickson' plum. Further the flesh color of 'Waplumone' is considered red while the seed parent 'Wickson' exhibits yellow flesh color.

BRIEF DESCRIPTION OF THE DRAWINGS

The accompanying drawing, which is provided, is a color photograph of four whole mature fruit harvested, from a tenth leaf tree displaying both the apical and basal fruit aspects. As shown in the photograph, one mature fruit is bisected transversely through the sagittal plane, which reveals the flesh color (see top fruit). Three fruit are also shown to display the apical aspect (second fruit from the top), the basal aspect (third fruit from the top), and the basal aspect with cutin (bloom) removed (bottom fruit). The external coloration of the fruit as shown in the photograph is sufficiently matured for harvesting and shipment. Additionally, the photograph displays a sample vegetative shoot bearing typical leaves and a typical stone with the flesh removed. The colors in these photographs are as nearly true as is reasonably possible in a color representation of this type. Due to chemical development, processing and printing, the leaves and fruit depicted in these photographs may, or may not, be accurate when compared to the actual specimen. For this reason, future color references should be made to the color plates (Royal Horticultural Society, Fourth Edition, 2001) and descriptions provided, hereinafter.

NOT A COMMERCIAL WARRANTY

The following detailed description has been prepared to solely comply with the provisions of 35 U.S.C. § 112 and does not constitute a commercial warranty (either expressed or implied) that the present variety will in the future display all the botanical, pomological, or other characteristics as set forth hereinafter. Therefore, this disclosure may not be relied upon to support any future legal claims including, but not limited to, breach of warranty of merchantability, fitness for any purpose, or non-infringement which is directed, in whole or in part, to the present variety.

DETAILED DESCRIPTION

Referring more specifically to the pomological details of this new and distinct variety of plum tree, the following has been observed during the tenth fruiting season and under the ecological conditions prevailing at the orchards of the assignee, which are located near the town of Fowler, county of Fresno, state of California. All major color code designations are by reference to the R.H.S. Colour Chart (Royal Horticultural Society, Fourth Edition, 2001) provided by The Royal Horticultural Society of Great Britain. Common color names are also occasionally used.

Tree:

*Size.*—Generally considered medium in its growth pattern as compared to other common commercial plum cultivars ripening in the late season of maturity. The tree of the present variety was pruned to a height of about 250.0 cm to about 300.0 cm at commercial maturity. Fruit size can vary with crop load and the conditions under which the fruit and tree are grown.

*Width.*—Approximately 290.0 cm.

*Vigor.*—Considered moderately vigorous. The present plum tree variety grew from about 135.0 cm to about 150.0 cm in height during the first growing season. The new variety was pruned to a height of approximately 150.0 cm during the first dormant season, and primary scaffolds were then selected for the desired tree structure.

*Productivity.*—Productive. Fruit set generally varies from more than the desired crop load to levels much higher than desired amounts when the new variety is grown in a suitable horticultural zone when a compatible, coincident pollen source is provided and under appropriate commercial conditions. The fruit set is spaced by thinning to develop the remaining fruit into the desired market-sized fruit. The number of the fruit set varies with the prevailing climatic conditions and the cultural practices employed.

*Fruit bearing.*—Regular. Fruit set has been more than adequate during the previous years of observation, and thinning was necessary during the past 8 years on both the original seedling and on subsequent asexually reproduced trees.

*Tree form.*—Upright and slightly spreading when pruned into a vase shape.

*Density.*—Considered moderately dense.

*Hardiness.*—The present tree was grown and evaluated in USDA Hardiness Zone 9. The calculated winter chilling requirements of the new tree is approximately 500 hours at a temperature below 7.0 degrees C. The present variety appears to be hardy under typical central San Joaquin Valley climatic conditions.

Trunk:

*Diameter.*—Approximately 24.0 cm in diameter when measured approximately 15.5 cm above the soil level. This measurement was taken at the beginning of the 8th growing season.

*Bark texture.*—Considered moderately rough with folds of papery scarfskin being present.

*Lenticels.*—Numerous flat, oval lenticels are present on the trunk, with approximately 3 lenticels per centimeter squared. The lenticels range in size from about 2.5 mm to about 4.5 mm in width and between about 1.0 mm and about 2.0 mm in height and have a yellow/orange color (approximately RHS Greyed-Orange Group 163 B). The development and size of the trunk lenticels can be influenced, to some degree, by the ambient growing conditions and are not, necessarily, a dependable characteristic of this variety. As trees of this variety mature, lenticels are present, but they are generally covered by increasing layers of cork (mature bark) and therefore become less apparent with advancing tree maturity.

*Lenticel color.*—Considered an orange brown (RHS Greyed-Orange Group 165 B).

*Bark coloration.*—Variable, but it is generally considered to be a greyed silver (RHS Greyed-Green Group 198 A).

Branches:

*Size.*—Considered medium large for the variety.

*Diameter.*—Average as compared to other plum varieties. The branches have a diameter of about 12.0 cm when measured during the 8th year after grafting.

*Flowering shoot thickness.*—Average for the species. Generally, the most consistent flower bud development and, therefore, potential fruiting sites occur occasionally on annual shoots which are about 9.0 mm in diameter or larger, but the vast majority of the fruit is borne on 2 to 5-year-old spurs.

*Surface texture.*—Average and appearing relatively smooth but with more furrowing on wood which is several years old. Lenticels are prevalent within the internodal margins. There are approximately 3 to 4 lenticels present in the internodal space, each with a flattened oval shape and oriented horizontally. the lenticels are about 2.0 mm to about 2.5 mm in width, about 1.0 mm in height, and have a muted light-brown color (approximately RHS Greyed-Orange Group 165 A).

*Crotch angles.*—Primary branches are considered variable and are usually growing at an angle of about 45 degrees when measured from a horizontal plane.

*Current season shoots.*—Surface texture — Substantially glabrous.

*Internode length.*—Approximately 2.5 cm to approximately 3.0 cm.

*Color of mature branches.*—Approximately Greyed Green (RHS Greyed-Green Group 198 C).

*Current season's shoots.*—Color. — Pinkish green (RHS Greyed-Orange Group 176 C).

Leaves:

*Size.*—Considered somewhat broad for the species. Leaf measurements have been taken from vigorous, upright, current-season growth at approximately mid-shoot.

*Leaf arrangement.*—Leaves and their attachment to the stem are arranged in a 4:1 sprial rotation as is typical in the *Prunus* genera. The 4 buds/nodes/leaf attachments are oriented such that the 4 nodes/leaves occur with a 360-degree vertical rotation of the stem and branch.

*Leaf length.*—About 95.0 mm to about 110.0 mm (including the petiole).

*Leaf Width.*—About 45.0 mm to about 50.0 mm.

*Leaf base-shape.*—The leaves generally exhibit unequal marginal symmetry relative to the leaf longitudinal axis.

*Leaf form.*—Lanceolate.

*Leaf tip form.*—Acuminate.

*Leaf color.*—Upper Leaf Surface — Medium green (approximately RHS Green Group 137 C).

*Leaf texture.*—Upper Leaf Surface — Glabrous. Lower Leaf Surface — Glabrous.

*Leaf color.*—Lower Leaf Surface — Deep green (approximately RHS Green Group 136 B).

*Leaf venation.*—Pinnately veined.

*Mid-vein.*—Color — Considered a pinkish brown (approximately RHS Greyed-Purple Group 185 D).

*Leaf margins.*—Gently undulating. Form. — Considered crenulate. Uniformity. — Generally uniform.

*Leaf petioles.*—Form. — Considered canaliculated and having a more pronounced trough when viewed from the dorsal aspect. The petiole margin is considered rounded when viewed from the ventral aspect. Size. — Considered medium large for the species. Length. — About 9.0 mm to about 12.0 mm. Diameter. — About 2.0 mm. Color. — A greenish pink (approximately RHS Greyed-Purple Group 182 C). Texture. — Glabrous. Strength. — Durable for species until senescence.

*Leaf glands.*—Size. — Considered relatively small for the species; approximately 1.5 mm in width and about 1.5 mm in height. Number. — Generally, one or, less commonly, two glands per marginal side are found. Observations of more than two glands per marginal side are very uncommon. Type. — Glands located at or near the base of the leaf are predominantly globose in shape. Color. — Considered a yellowed green (approximately RHS Yellow-Green Group 151 A). Typically, the coloration of the glands darkens and occasionally begins to desiccate relatively early in the growing season.

*Leaf stipules.*—Size. — Medium large for this variety with a length of about 8.0 mm to about 12.0 mm and a width of about 1.5 mm. Number. — Typically, 2 per leaf bud and occasionally from 4 to 6 per shoot tip. Form. — Lanceolate in form and having a serrated marginal edge. Color. — Green (approximately RHS Green Group 137 C) when young, but graduating to a brown color (approximately RHS Greyed-Orange Group 165 A) with advancing senescence. The leaf stipules are generally considered to be early deciduous.

Flower buds:

*Hardiness.*—No winter injury (floral bud death) has been noted during the last several years of observation in the central San Joaquin Valley. The new variety of plum tree has not been intentionally subjected to drought, cold, or heat stress and, therefore, information regarding these traits is not available.

*Flower bud.*—Size — Variable, medium small dependent on the state of maturity. The flower buds as described were observed approximately 7 days prior to bloom. Length — Approximately 7.0 mm to approximately 9.0 mm. Diameter — Approximately 6.0 mm. Surface Texture. — Pubescent. Orientation. — Considered appressed but appear less so as the blossoms near opening.

*Bud scale color.*—Approximately RHS Greyed-Orange Group 177 B.

Flowers:

*Date of first bloom.*—Observed on Feb. 23, 2019. Blooming Time. — Considered average to slightly early mid-bloom in relative comparison to other commercial plum cultivars grown in the central San Joaquin Valley. The date of full bloom was observed on Feb. 28, 2019. The date of full bloom varies slightly with climatic conditions and prevailing cultural practices. Duration of Bloom. — Approximately 12 or more days. This characteristic varies slightly with the prevailing climatic conditions.

*Flower class.*—Considered a perfect flower, complete and perigynous.

*Flower type.*—The variety is considered to have a showy type flower. Flower Size. — Considered medium for the species. The flower diameter at full bloom is approximately 30.0 mm to approximately 32.0 mm. Flower Depth. — The flower depth is about 6.0 mm to about 7.0 mm measured along the vertical plane of the flower from the stamen tip to the pedicle base.

*Bloom quantity.*—Considered abundant with approximately 2 to 6 flowers present per spur cluster, which may vary depending on the age of the tree, the tree's vigor, the length and age of the fruiting spur, and exposure to sunlight.

*Flower bud density.*—Generally considered dense. Flower Bud Frequency. — Generally, two flower buds appear per node and, occasionally, one flower bud per node is observed. Multiple flower buds are present on mature fruiting spurs.

*Petal size.*—Generally considered medium for the species. Petal Length. — Approximately 12.0 mm to approximately 15.0 mm. Petal Width. — Approximately 9.0 mm to approximately 11.0 mm.

*Petal form.*—Considered ovate.

*Petal count.*—Nearly always 5.

*Petal texture.*—Upper Petal Texture. — Very finely pubescent, satin like. Lower Petal Texture. — Very finely pubescent, satin like.

*Petal color.*—The dorsal surface of the flower petal is considered a bright white at the popcorn stage and throughout the bloom period (RHS White Group 155 D). The ventral surface of the flower petal is also RHS White Group 155 D. The petal surface is finely pubescent and satiny.

*Fragrance.*—Slight.

*Petal claw.*—Form. — The claw is considered ovate and is generally large relative to the petal size. Length. — Approximately 10.0 mm. Width. — Approximately 5.0 mm.

*Petal margins.*—Generally, slightly undulate. The petal margin is entire at the apex.

*Petal apex.*—Entire.

*Petal base.*—Considered even and equal in both margins.

*Flower pedicel.*—Length. — Considered medium with an approximate length of about 1.5 mm to about 2.5 mm. Diameter. — About 1.0 mm to about 1.5 mm. Color. — A medium brown (approximately RHS Greyed-Orange Group 177 C) depending on pedicel and fruit maturity and timing of visual observance. Strength. — Tenacious. Average for the species. Texture. — Generally smooth to slightly undulate.

*Floral nectaries.*—Color. — Considered a pale green (approximately RHS Yellow-Green Group 145 B).

*Calyx.*—Surface Texture. — Generally glabrous. Color. — Approximately RHS Yellow-Green Group 145 A.

*Sepals.*—Upper Surface Texture. — Moderately pubescent, Satiny. Lower Surface Texture. — Glabrous. Number. — 5 sepals. Size. — Considered medium. Sepal Length. — Approximately 4.0 mm to approximately 5.0 mm. Sepal Width. — Approximately 3.0 mm. Sepal Shape. — Generally obovate. Sepal Apex. — Considered to have a smooth and entire margin. Sepal Margin. — Considered smooth and entire. Sepal Color. — Approximately RHS Yellow-Green Group 145 A. The internal surface of the sepal is considered a very pale green (approximately RHS Yellow-Green Group 150 D).

*Anthers.*—Generally. — Average in size with a length of about 1.0 mm, a width of about 0.75 mm, and a depth of about 0.5 mm. Color. — White (approximately RHS White Group 155 D). Position Relative to Stigma. — Generally, the stigma is superior to the anthers by about 1.0 mm to about 2.0 mm. Position Relative to Petals. — At flower maturity, the stamens grow to be approximately 4.0 mm to approximately 6.0 mm superior to the base of the petals.

*Pollen production.*—Pollen is abundant and has a yellow color (approximately RHS Yellow-Orange Group 17 C).

*Fertility.*—Self-unfertile. Pollen allele grouping D2-D7 according to one allele classification test. Prospective *Prunus salicina* plum varieties as pollinators could be 'Santa Rosa' (unpatented), 'Primetime' (U.S. Plant Pat. No. 9,022), 'Fortune' (unpatented), or 'Golden Japan' (unpatented).

*Filaments.*—Size. — Approximately 8.0 mm to approximately 10.0 mm in length. Color. — Considered a light greenish white (RHS Yellow-Green Group 145 D).

*Pistil.*—Number. — Usually one and, only rarely, more than one. Generally. — Considered medium in size. Length. — Approximately 9.0 mm to about approximately 12.0 mm in length including the ovary. Ovary. — Glabrous. Color. — Considered a very pale green (approximately RHS Yellow-Green Group 149 C). Surface Texture. — The variety has a long glabrous pistil.

Fruit:

*Maturity when described.*—Firm ripe condition (shipping ripe).

*Date of first picking.*—Approximately Jul. 2, 2019.

*Date of last picking.*—Jul. 12, 2019. The date of harvest can vary with the prevailing climatic conditions, crop loads, and the current climatic and cultural practices.

*Size.*—Generally — Considered medium to medium small.

*Average cheek diameter.*—About 45.0 mm to about 58.0 mm.

*Average axial diameter.*—About 43.0 mm to about 55.0 mm.

*Typical weight.*—Approximately 165.0 grams. The fruit size and weight can vary and are dependent on the prevailing cultural practices and growing conditions and, therefore, are not particularly distinctive of the new variety.

*Fruit soluble solids.*—Approximately 22.0 degrees Brix to approximately 27.0 degrees Brix. Fruit sugar levels can vary significantly depending on fruit maturity and local and seasonal climatic conditions.

*Fruit firmness.*—Fruit flesh pressures generally averaged 12.0 pounds (about 5.44 kg) at the time the fruit was analyzed.

*Titratable acidity.*—Approximately 0.5 to approximately 0.6 at commercial harvest maturity.

*Fruit form.*—Generally — Considered oblate. The fruit is generally very uniform in symmetry.

*Mucron tip.*—Absent.

*Fruit suture.*—No stitching exists along the suture line.

*Suture.*—Color — Generally, the fruit appears blushed to the same degree as the skin (as described below).

*Ventral surface.*—Form — Considered even and uniform in appearance when it is viewed from the lateral, sutural plane.

*Apex.*—Shape — Rounded to slightly retuse.

*Base.*—Shape — Generally smooth and slightly retuse.

*Stem cavity.*—Generally — It extends in a rounded circular form which is generally considered uniform. The stem cavity is rounded but slightly extended toward the suture. The average depth of the stem cavity is about 5.0 mm to about 7.0 mm. The average width of the stem cavity is about 12.0 mm. The average length of the stem cavity, when measured in the sutural plane is about 14.0 mm.

*Fruit skin.*—Thickness. — Considered medium in thickness, and tenacious to the flesh. Surface Texture. — Glabrous. Abundant smooth lenticels are present under the skin surface. Taste. — Non-astringent. Tendency to crack. — Radial cracking can be observed over the shoulders of the fruit at very high maturities or if fruit is subjected to rainfall when nearing harvest maturity. Lenticels. — Subcutaneous lenticels are present and are more numerous in the basal hemisphere with approximately 8 to 15 lenticels per centimeter squared. The lenticels are smooth and generally do not protrude through the fruit surface until fruit maturity is well past commercial harvest conditions. The lenticels are about 0.5 mm to about 1.0 mm in diameter and are considered to have a dull olive brown color (approximately RHS Grey-Brown N199 A).

*Fruit skin color.*—

*Fruit color.*—Generally speaking, the color of the fruit skin is mottled. A golden green ground color is the overall ground color (described below) with sections of a dull reddish hue (described below) present throughout the fruit skin surface, but often more present on the surface that is more exposed to sunlight. Fruit color would most resemble the 'Mariposa' plum (Luther Burbank introduced from Japan, 1885).

*Blush color.*—It exhibits a mixture of a dull red blush (approximately RHS Greyed-Red Group 178 B) more typically present on the portions of the fruit facing the sunlight. The blush of the fruit typically covers approximately 25% to approximately 45% of the fruit skin surface. The percentage of the blush on the fruit skin surface can vary and is generally dependent upon the fruit's exposure to direct sunlight, specific fruit maturity, and the prevailing ecological and cultural conditions under which the fruit was grown.

*Ground color.*—A greenish-golden (approximately RHS Yellow-Green Group 155 C).

*Fruit glossiness.*—Fruit considered to be moderately glossy with a heavy bloom (cutin) layer covering the surface.

*Fruit stem.*—Size. — Medium in length, about 6.0 mm to about 8.0 mm. Diameter. — About 2.0 mm to about 3.0 mm. Color. — Pale yellow green (approximately RHS Yellow-Green Group N144 B).

*Fruit flesh.*—Ripening. — Considered even. Texture. — Firm, crunchy, juicy and dense. Considered non-melting in flesh classification. Fibers. — Present but not prominent. Aroma. — Slight. Eating Quality. — Considered Excellent. Flavor. — Excellent, complex flavor. Considered balanced with sweetness and acidity. Juice Production. — High. Brix. — About 22.0 degrees to about 27.0 degrees. This characteristic varies slightly with the number of fruits per tree, fruit position on the tree, the maturity of fruit when harvested, the prevailing cultural practices, and the ambient climatic conditions. Acidity. — Considered medium. Approximately 0.5 to approximately 0.6 titratable acidity at fruit harvest. Acid levels assayed from fruit flesh can vary with fruit maturity, length of time in cold storage, sunlight exposure, and climatic, regional, seasonal, and cultural influences. Flesh Color. — It is considered pinkish white (approximately RHS Greyed-Red Group 180 C) to a deeper reddish color (approximately RHS Greyed-Red Group 181 A) when observed closer to fruit maturity.

Stone:

*Type.*—Considered a tight freestone.

*Size.*—It is generally considered to be medium small for the species. The stone size varies significantly depending upon the tree vigor, the crop load, and the prevailing growing and cultural conditions under which the tree was grown.

*Length.*—Average, about 18.0 mm to about 21.0 mm.

*Width.*—Average, about 16.0 mm to about 18.0 mm.

*Diameter.*—Average, about 8.0 mm to about 12.0 mm.

*Form.*—Roughly ovoid.

*Stone base.*—Shape — The stone is considered ovoid.

*Apex.*—Shape — The stone often exhibits a reasonably small acute tip.

*Stone surface.*—Surface Texture — Considered relatively smooth. Ridges. — Surface ridging is generally not present. Ventral Edge. — The ventral edge is generally described as having adjoining ridges formed from each hemisphere and a more prominent ridge in the ventral suture margin. Dorsal edge. — Shape — Generally considered even without ridging.

*Stone color.*—The color of a mature, dry stone is generally considered a pale light brown (approximately RHS Yellow-White Group 158 A).

*Tendency to split.*—Splitting has rarely been noted.

*Kernel.*—Length. — Approximately 12.0 mm to approximately 15.0 mm. Width. — Approximately 14.0 mm to approximately 16.0 mm. Thickness. — Approximately 4.0 mm to approximately 6.0 mm. Size. — The kernel is considered medium small. Form. — Considered generally ovoid to rounded in shape. Kernel Surface Texture. — Kernel pellicle is shortly pubescent. Color. — A dark tan (RHS Greyed-Orange Group 164 B).

*Use.*—The present variety 'Waplumone' is considered to be a plum tree of early mid-season of maturity, which produces fruit which are considered to be firm, attractively colored, and useful for both local and long-distance shipping.

*Keeping quality.*—Appears excellent. The fruit of the present variety has stored well for periods of up to 30 days after harvest at 1.0 degree Celsius.

*Shipping quality.*—Good. The fruit of the new plum tree variety showed minimal bruising of the flesh or skin damage after being subjected to normal harvesting and packing procedures.

*Resistance to insects and disease.*—No susceptibilities were noted. The present variety has not been intentionally tested to expose or detect any susceptibilities or resistances to any known plant, fruit diseases, insect, frost, winter injury, or other environmental factors.

Although the new variety of plum tree possesses the described characteristics when grown under the ecological conditions prevailing near Fowler, Calif., in the Central part of the San Joaquin Valley of California, variations of the usual magnitude and characteristics incident to changes in growing conditions, fertilization, nutrition, pruning, pest control, frost, climatic variables, and changes in horticultural management are to be expected.

Having thus described and illustrated our new variety of plum tree, what we claim is new, and desire to secure by plant Letters Patent is:

1. A new distinct variety of plum tree substantially as illustrated and described, and which is characterized principally as to novelty by producing an attractively colored red-fleshed, freestone plum which is mature for harvesting and shipment approximately July 2 to July 12 under the ecological conditions prevailing in the San Joaquin Valley of central California.

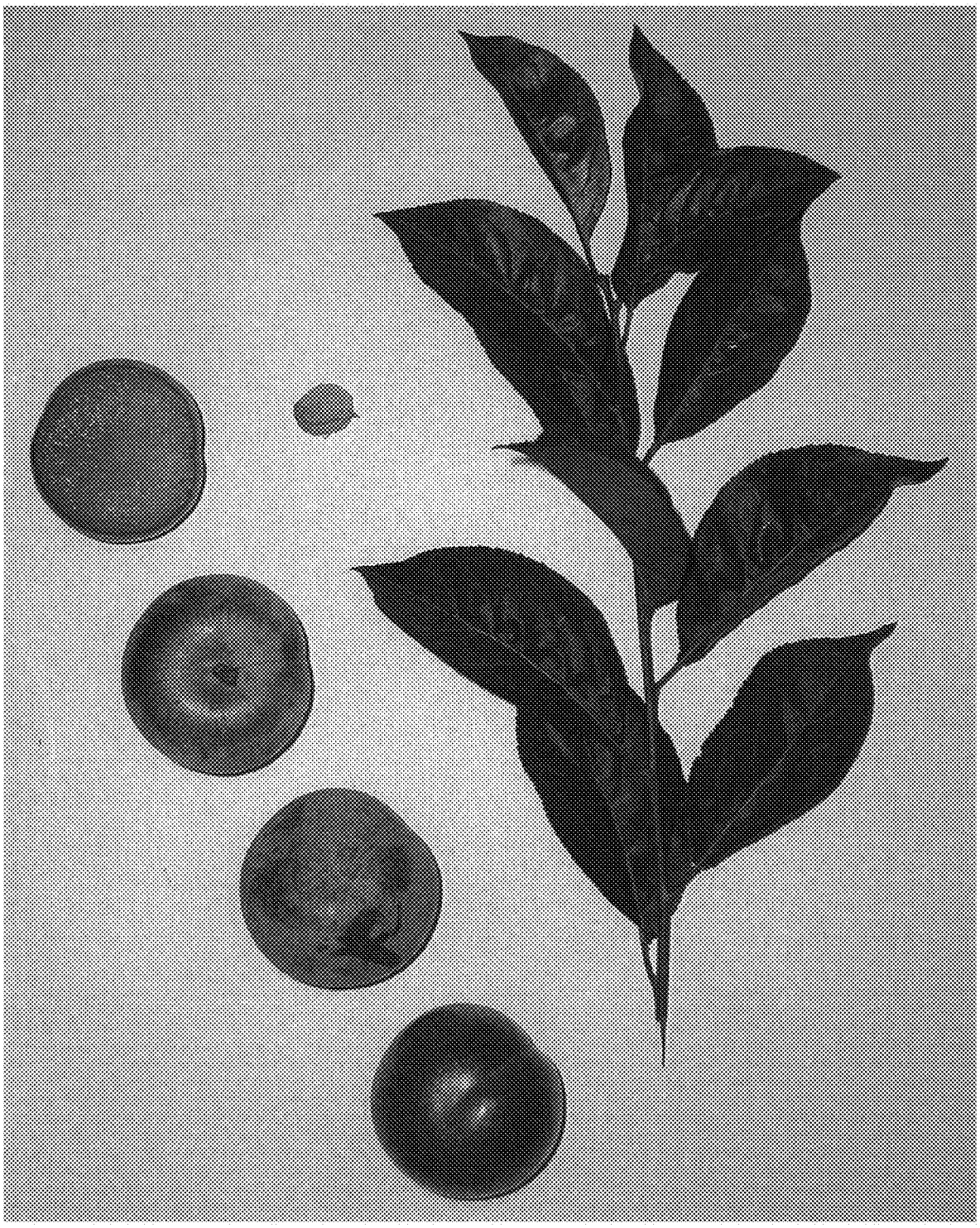

* * * * *